United States Patent
Bayer et al.

(10) Patent No.: US 12,358,848 B2
(45) Date of Patent: *Jul. 15, 2025

(54) METHOD OF FORMING A MYCOLOGICAL PRODUCT

(71) Applicant: Ecovative LLC, Green Island, NY (US)

(72) Inventors: Eben Bayer, Troy, NY (US); Gavin McIntyre, Troy, NY (US)

(73) Assignee: Ecovative LLC, Green Island, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/606,318

(22) Filed: Mar. 15, 2024

(65) Prior Publication Data
US 2025/0011251 A1    Jan. 9, 2025

Related U.S. Application Data

(60) Continuation of application No. 16/661,726, filed on Oct. 23, 2019, now Pat. No. 11,932,584, which is a division of application No. 13/856,086, filed on Apr. 3, 2013, now Pat. No. 10,525,662, which is a division of application No. 12/001,556, filed on Dec. 12, 2007, now Pat. No. 9,485,917.

(60) Provisional application No. 60/927,458, filed on May 3, 2007, provisional application No. 60/875,243, filed on Dec. 15, 2006.

(51) Int. Cl.
| | |
|---|---|
| C05D 9/00 | (2006.01) |
| A01G 18/00 | (2018.01) |
| A01G 18/40 | (2018.01) |
| A01G 18/50 | (2018.01) |
| A01G 18/64 | (2018.01) |
| B32B 5/02 | (2006.01) |
| B32B 5/16 | (2006.01) |
| C12N 1/14 | (2006.01) |
| C12N 11/14 | (2006.01) |

(52) U.S. Cl.
CPC .............. *C05D 9/00* (2013.01); *A01G 18/00* (2018.02); *A01G 18/40* (2018.02); *A01G 18/50* (2018.02); *A01G 18/64* (2018.02); *B32B 5/02* (2013.01); *B32B 5/16* (2013.01); *C12N 1/14* (2013.01); *C12N 11/14* (2013.01); *B32B 2439/00* (2013.01); *Y10T 428/1348* (2015.01); *Y10T 428/249921* (2015.04); *Y10T 428/31504* (2015.04)

(58) Field of Classification Search
None
See application file for complete search history.

(56) References Cited

U.S. PATENT DOCUMENTS

| | | | |
|---|---|---|---|
| 4,722,159 A | 2/1988 | Watanabe et al. | |
| 9,485,917 B2 * | 11/2016 | Bayer | B32B 5/02 |
| 10,525,662 B2 * | 1/2020 | Bayer | B32B 5/16 |
| 11,932,584 B2 * | 3/2024 | Bayer | A01G 18/50 |

FOREIGN PATENT DOCUMENTS

| | | |
|---|---|---|
| FR | 2603767 A1 | 3/1988 |
| FR | 2676158 A1 | 11/1992 |
| FR | 2723506 A1 | 2/1996 |
| JP | 2008-154463 A | 7/2008 |
| JP | 5156243 B2 | 3/2013 |
| RU | 79748 | 1/2009 |

\* cited by examiner

*Primary Examiner* — Blaine Lankford
(74) *Attorney, Agent, or Firm* — Dority & Manning, P.A.

(57) ABSTRACT

The method grows a mycelial mass over a three-dimensional lattice such that a dense network of oriented hyphae is formed on the lattice. Growth along the lattice results in mycelium composite with highly organized hyphae strands and allows the design and production of composites with greater strength in chosen directions due to the organized nature of the supporting mycelia structure.

17 Claims, 5 Drawing Sheets

METHOD OF FORMING A MYCOLOGICAL PRODUCT

This is a Division of U.S. Ser. No. 13/856,086, filed Apr. 3, 2013, which is a Division of U.S. Ser. No. 12/001,556, filed Dec. 12, 2007, now U.S. Pat. No. 9,485,917.

This invention claims the benefit of Provisional Patent Application No. 60/875,243 filed Dec. 15, 2006, and Provisional Patent Application No. 60/927,458 filed May 3, 2007, the contents of each being incorporated by reference herein.

This invention relates to a method of forming a mycological product.

BACKGROUND OF THE INVENTION

Materials are produced today using a range of processes ranging from time intensive outdoor growth and harvesting to energy intensive factory centric production. As demand for raw goods and materials rise, the associated cost of such materials rises. This places greater pressure on limited raw materials, such as minerals, ores, and fossil fuels, as well as on typical grown materials, such as trees, plants, and animals. Additionally, the production of many materials and composites produces significant environmental downsides in the form of pollution, energy consumption, and a long post use lifespan.

Conventional materials such as expanded petroleum based foams are not biodegradable and require significant energy inputs to produce in the form of manufacturing equipment, heat and raw energy.

Conventionally grown materials, such as trees, crops, and fibrous plants, require sunlight, fertilizers and large tracts of farmable land.

Finally, all of these production processes have associated waste streams, whether they are agriculturally or synthetically based.

Fungi are some of the fastest growing organisms known. They exhibit excellent bioefficiency, of up to 80%, and are adept at converting raw inputs into a range of components and compositions. Fungi are composed primarily of a cell wall that is constantly being extended at the tips of the hyphae. Unlike the cell wall of a plant, which is composed primarily of cellulose, or the structural component of an animal cell, which relies on collagen, the structural oligosaccharides of the cell wall of fungi relay primarily on chitin. Chitin is strong, hard substance, also found in the exoskeletons of arthropods. Chitin is already used within multiple industries as a purified substance. These uses include: water purification, food additives for stabilization, binders in fabrics and adhesives, surgical thread, and medicinal applications.

Given the rapid growth times of fungi, its hard and strong cellular wall, its high level of bioeffeciency, its ability to utilize multiple nutrient and resource sources, and, in the filamentous types, its rapid extension and exploration of a substrate, materials and composites, produced through the growth of fungi, can be made more efficiently, cost effectively, and faster, than through other growth processes and can also be made more efficiently and cost effectively then many synthetic processes.

Numerous patents and scientific procedure exists for the culturing of fungi for food production, and a few patents detail production methods for fungi with the intent of using its cellular structure for something other than food production. For instance U.S. Pat. No. 5,854,056 discloses a process for the production of "fungal pulp", a raw material that can be used in the production of paper products and textiles.

Accordingly, it is an object of the invention to provide method of producing a mycological product in an economical manner.

Briefly, the invention provides a method that uses the growth of hyphae, collectively referred to as mycelia or mycelium, to create materials composed of the fungi cellular tissue.

The method employs a step for growing filamentous fungi from any of the divisions of phylum Fungi. The examples that are disclosed focus on composites created from basidiomycetes, e. g., the "mushroom fungi" and most ectomycorrhizal fungi. But the same processes will work with any fungi that utilizes filamentous body structure. For example, both the lower fungi, saphrophytic oomycetes, the higher fungi, divided into zygomycetes and endo-mycorrhizal fungi as well as the ascomycetes and deutoeromycetes are all examples of fungi that possess a filamentous stage in their life-cycle. This filamentous stage is what allows the fungi to extend through its environment creating cellular tissue that can be used to add structural strength to a loose conglomeration of particles, fibers, or elements.

These and other objects and advantages will become more apparent from the following detailed description taken in conjunction with the accompanying drawings wherein.

Figure 1:
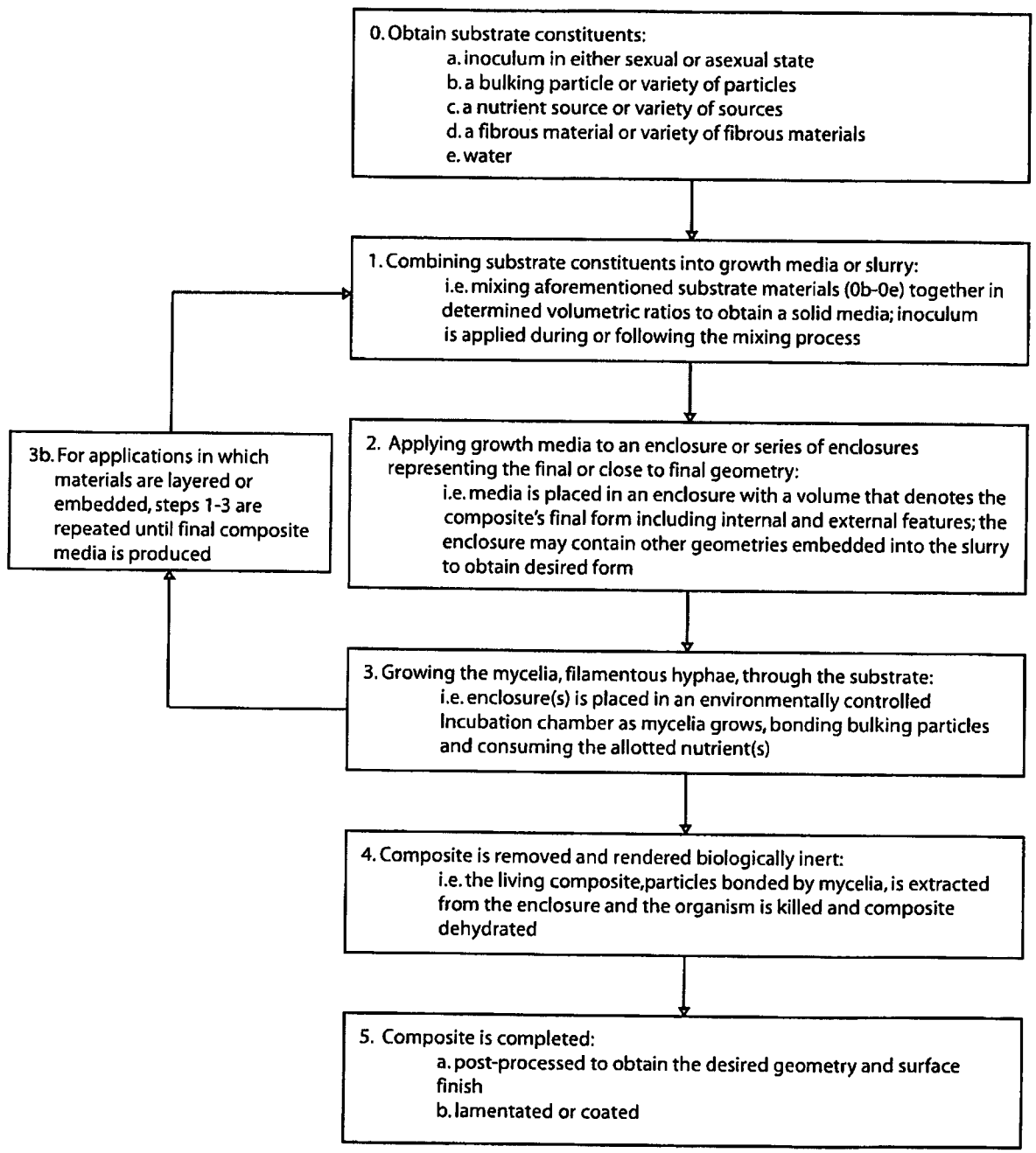
FIG. 1 illustrates a simplified flow chart of a method employed for making a fungi bonded material in accordance with the invention.

Referring to FIG. 1, the method of making a self-supporting structural material is comprised of the following steps.

0. Obtain substrate constituents, i.e. inoculum in either a sexual or asexual state, a bulking particle or a variety of bulking particles, a nutrient source or a variety of nutrient sources, a fibrous material or a variety of fibrous materials and water.
1. combining the substrate constituents into a growth media or slurry by mixing the substrate materials together in volumetric ratios to obtain a solid media while the inoculum is applied during or following the mixing process.
2. applying the growth media to an enclosure or series of enclosures representing the final or close to final geometry. The media is placed in an enclosure with a volume that denotes the composite's final form including internal and external features. The enclosure may contain other geometries embedded in the slurry to obtain a desired form.
3. growing the mycelia, i.e. filamentous hyphae, through the substrate. The enclosure is placed in an environmentally controlled incubation chamber as mycelia grows bonding the bulking particles and consuming the allotted nutrient(s).

3a. repeating steps 1-3 for applications in which materials are layered or embedded until the final composite media is produced.

4. removing the composite and rendering the composite biologically inert. The living composite, i.e. the particles bonded by the mycelia, is extracted from the enclosure and the organism is killed and the composite dehydrated.

5. completing the composite. The composite is post-processed to obtain the desired geometry and surface finish and laminated or coated.

The inoculum is produced using any one of the many methods known for the cultivation and production of fungi including, but not limited to, liquid suspended fragmented mycelia, liquid suspended spores and mycelia growing on solid or liquid nutrient.

Inoculum is combined with the engineered substrate, which may be comprised of nutritional and non-nutritional particles, fibers, or other elements. This mixture of inoculum and substrate is then placed in an enclosure.

In step 3, hyphae are grown through the substrate, with the net shape of the substrate bounded by the physical dimensions of the enclosure. This enclosure can take on any range of shapes including rectangles, boxes, spheres, and any other combinations of surfaces that produce a volume. Growth can occur both inside the enclosure and outside of the enclosure depending on desired end shape. Similarly, multiple enclosures can be combined and nested to produce voids in the final substrate. Other elements embedded with the slurry may also become integrated into the final composite through the growth of the hyphae.

The hyphae digest the nutrients and form a network of interconnected mycelia cells growing through and around the nutrients and through and around the non-nutrient particles, fibers, or elements. This growth provides structure to the once loose particles, fibers, elements, and nutrients, effectively bonding them in place while bonding the hyphae to each other as well.

In step 4, the substrate, now held tightly together by the mycelia network, is separated from the enclosure, and any internal enclosures or elements are separated away, as desired.

The above method may be performed with a filamentous fungus selected from the group consisting of ascomycetes, basidiomycetes, deuteromycetes, oomycetes, and zygomycetes. The method is preferably performed with fungi selected from the class: Holobasidiomycete.

The method is more preferably performed with a fungus selected from the group consisting of:

*Pleurotus ostreatus*
*Agrocybe brasiliensis*
*Flammulina velutipes*
*Hypholoma capnoides*
*Hypholoma sublaterium*
*Marchella angusticeps*
*Macrolepiota procera*
*Coprinus comatus*
*Agaricus arvensis*
*Ganodermatsugae*
*Inonotus obliquus*

The method allows for the production of materials that may, in various embodiments, be characterized as structural, acoustical, insulating, shock absorbing, fire protecting, biodegrading, flexible, rigid, water absorbing, and water resisting and which may have other properties in varying degrees based on the selection of fungi and the nutrients. By varying the nutrient size, shape, and type, the bonded bulking particle, object, or fiber, size, shape, and type, the environmental conditions, and the fungi strain, a diverse range of material types, characteristics and appearances can be produced using the method described above.

The present invention uses the vegetative growth cycle of filamentous fungi for the production of materials comprised entirely, or partially of the cellular body of said fungi collectively known as mycelia.

Figure 2:
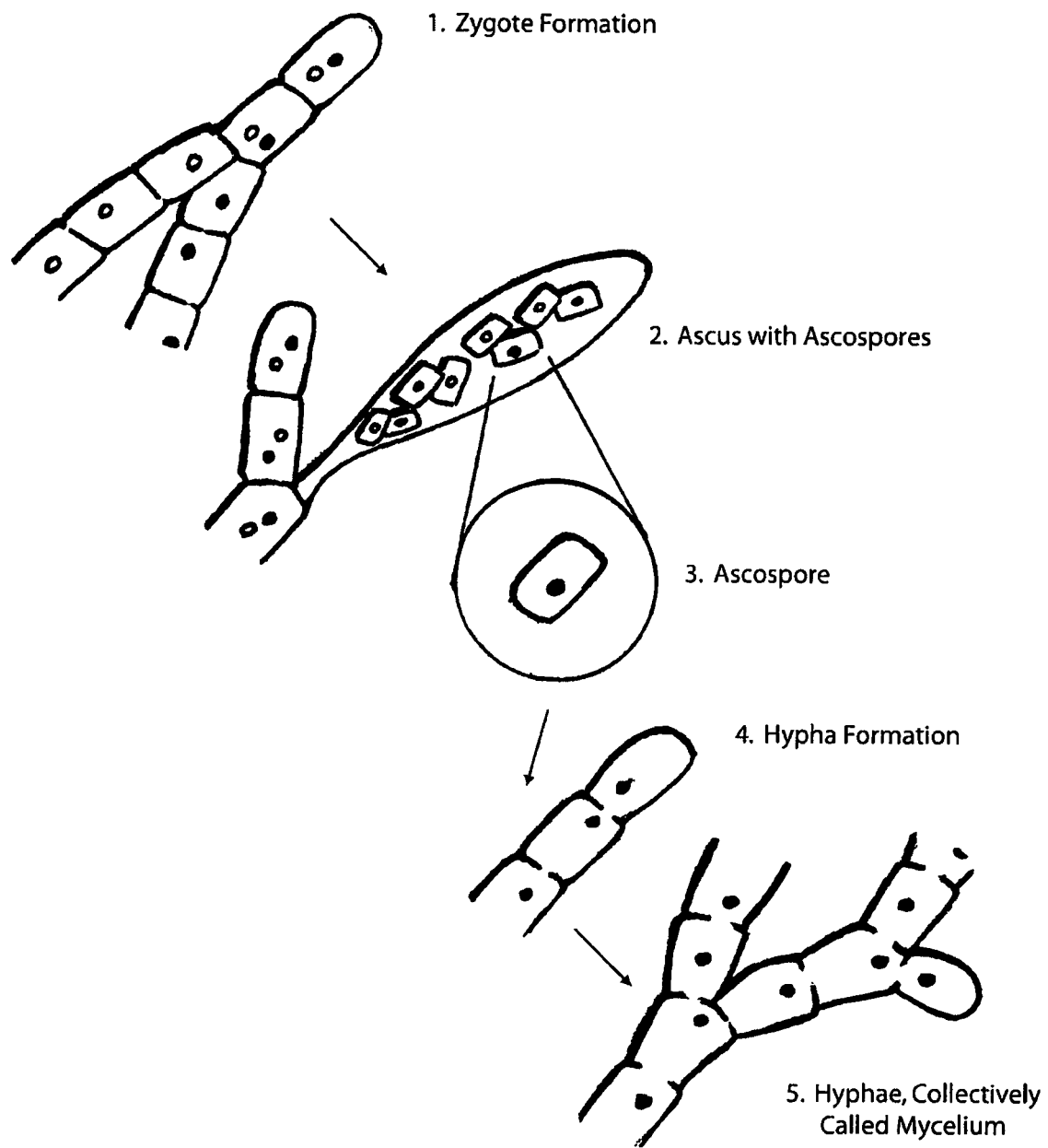
FIG. 2 illustrates a schematic life cycle of *Pleurotus ostreatus*.

FIG. 2 shows a schematic representation of the life cycle of *Pleareotus Ostreatus*, filamentous fungi. The area of interest for this invention is the vegetative state of a fungi's life cycle where a fungi is actively growing through the extension of its tube like hyphae.

In this Description, the following definitions are specifically used:

Spore: The haploid, asexual bud or sexual reproducing unit, or "seed", of a fungus.

Hyphae: The thread-like, cellular tube of filamentous fungi which emerge and grow from the germination of a fungal spore.

Mycelium: The collection of hyphae tubes originating from a single spore and branching out into the environment.

Inoculum: Any carrier, solid, aerated, or liquid, of a organism, which can be used to transfer said organism to another media, medium, or substrate.

Nutrient: Any complex carbohydrate, polysaccharide chain, or fatty group, that a filamentous fungi can utilize as an energy source for growth.

Fruiting Body: A multicellular structure comprised of fungi hyphae that is formed for the purpose of spore production, generally referred to as a mushroom.

Fungi Culturing for Material Production

Methodology

Procedures for culturing filamentous fungi for material production.

All methods disclosed for the production of grown materials require an inoculation stage wherein an inoculum is used to transport a organism into a engineered substrate. The inoculum, carrying a desired fungi strain, is produced in sufficient quantities to inoculate the volume of the engineered substrates; inoculation volume may range from as low as 1% of the substrates total volume to as high as 80% of the substrates volume. Inoculum may take the form of a liquid carrier, solid carrier, or any other known method for transporting a organism from one growth supporting environment to another.

Generally, the inoculum is comprised of water, carbohydrates, sugars, vitamins, other nutrients and the fungi. Depending on temperature, initial tissue amounts, humidity, inoculum constituent concentrations, and growth periods, culturing methodology could vary widely.

Grown Material Within an Enclosure

Figure 3:
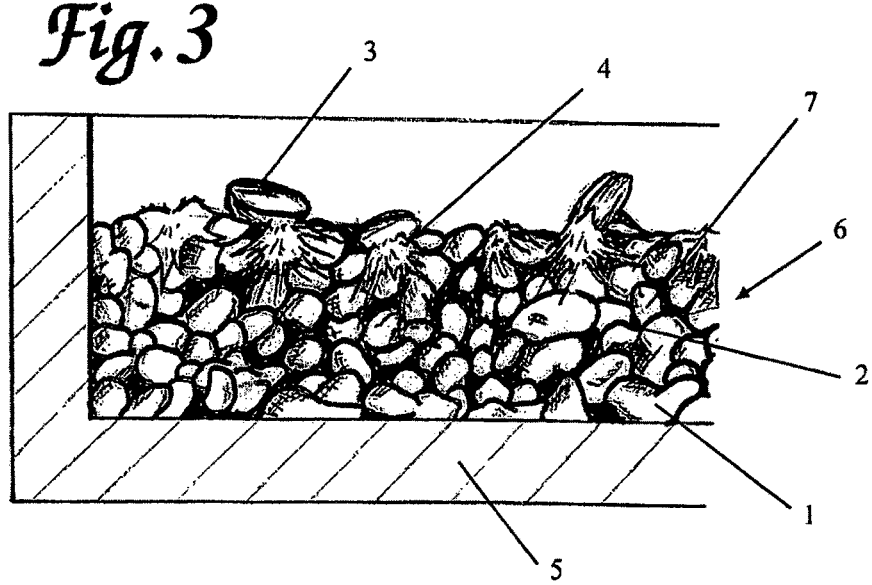
FIG. 3 illustrates an inoculated substrate before growth in an enclosure in accordance with the invention.

FIG. 3 shows a side view of one embodiment i.e. an insulating composite, just after inoculation has taken place.

In this embodiment, a group of nutritional particles 1 and a group of insulating particles 2 were placed in an enclosure 5 to form an engineered substrate 6 therein. The enclosure 5 has an open top and determines the final net shape of the grown composite. Thereafter, an inoculum 3 was applied directly to the surface of the engineered substrate 6.

Shortly after the inoculum 3 was applied to the surface, hyphae 4 were visible extending away from the inoculum 3 and into and around the nutritional particles 1 and insulating particles 2.

Figure 4:
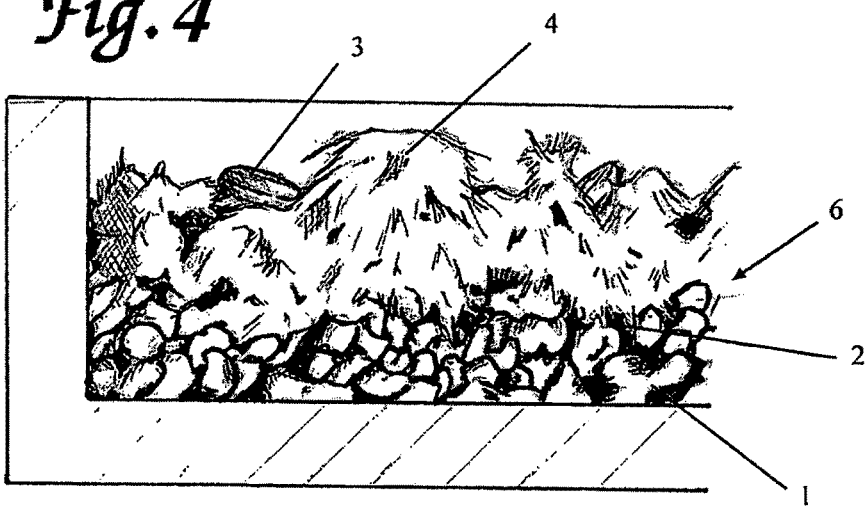
FIG. 4 illustrates an inoculated substrate after three days of growth in accordance with the invention.

FIG. 4 shows a side view of the same embodiment described above, i.e. an insulating composite, approximately 3 days after the inoculum 3 was applied to the surface of the engineered substrate 6. Hyphae 3 have now penetrated into the engineered substrate 6 and are beginning to bond insulating particles 2 and nutritional particles 1 into a coherent whole.

Figure 5:
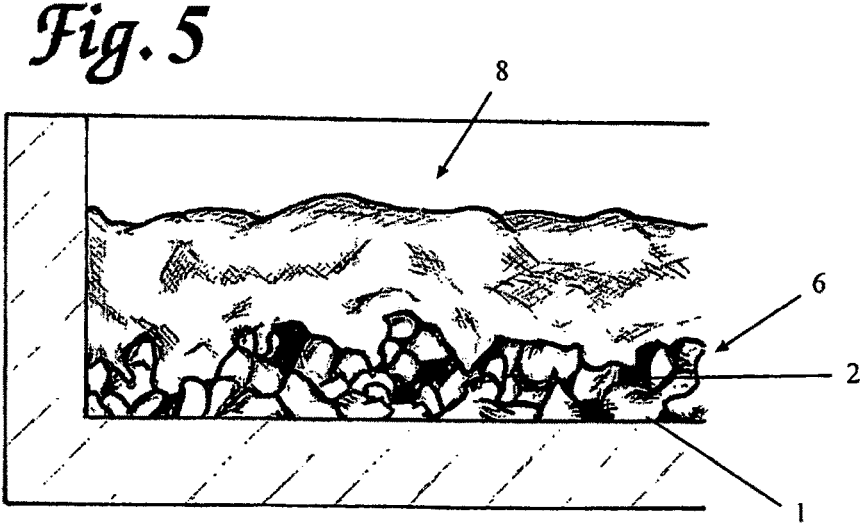
FIG. 5 illustrates an inoculated substrate nearing the end of the growth in accordance with the invention.

FIG. 5. shows a side view of the same embodiment of FIGS. 3 and 4, i.e. an insulating composite, approximately 7 days after the inoculum 3 was applied to the surface of the engineered substrate 6. Hyphae 3, collectively referred to as mycelia 7, have now fully colonized the top half of engineered substrate 6, bonding insulating particles 2 and nutritional particles 1 into a coherent whole.

Figure 6:
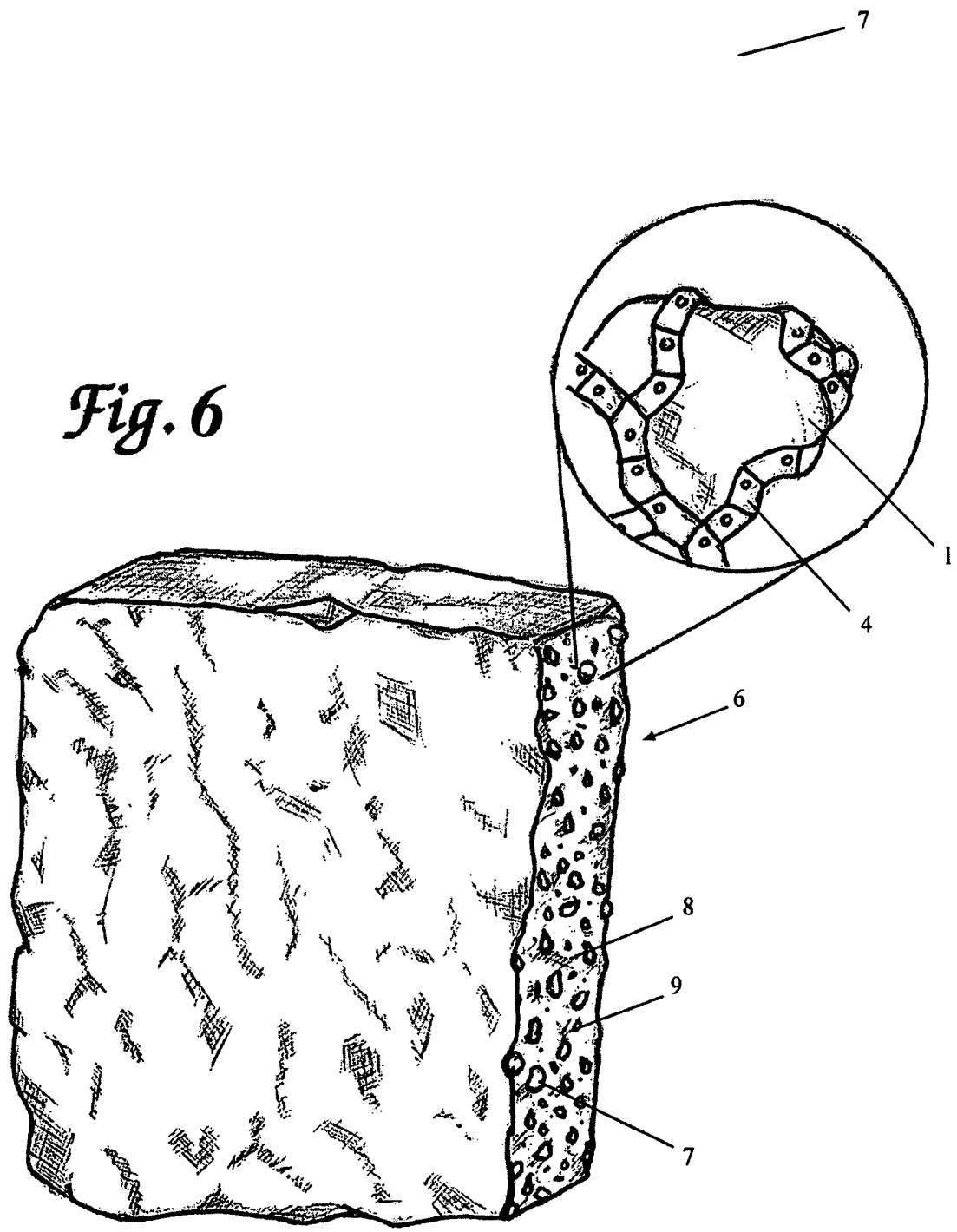
FIG. 6 illustrates a final composite of one embodiment composed of nutrient particles and a bulking particle in accordance with the invention.

FIG. 6 shows a side view of the same embodiments of FIGS. 3, 4 and 5, i.e. an insulating composite, after the engineered substrate 6 has been fully colonized and bonded by mycelia 7. A cutaway view shows a detail of a single insulating particle bound by a number of hyphae 4. Also shown within this embodiment are fibers 9 bound within mycelia 8.

Static Embodiment—Composite

FIG. 6 shows a perspective view of one embodiment of a mycelia bonded composite composed of nutritional particles, bulking particles, fibers, and insulating particles. In this embodiment of a mycelia bonded composite, the following growth conditions and materials were used: The engineered substrate was composed of the following constituents in the following percentages by dry volume:
 1. Rice Hulls, purchased from Rice World in Arkansas, 50% of the substrate.
 2. Horticultural Perlite, purchased from World Mineral of Santa Barbra, California, 15% of the substrate.
 3. DGS, dried distillers grains, sourced from Troy Grain Traders of Troy NY, 10% of the substrate.
 4. Ground cellulose, composed of recycled paper ground into an average sheet size of 1 mm×1 mm, 10% of the substrate.
 5. Coco coir, sourced from Mycosupply, 10% of the substrate.
 6. Inoculum composed of rye grain and inoculated with *Plearotus Ostreatus,* 3% of the substrate.
 7. Birch sawdust, fine ground, 2% of the substrate by volume.
 8. Tap water, from the Troy Municipal Water supply, was added until the mixture reached field capacity, an additional 30% of the total dry substrate volume was added in the form of water.

These materials were combined together in a dry mix process using a rotary mixer to fully incorporate the particles, nutrients, and fibers. Water was added in the final mixing stage. Total mixing time was 5 minutes.

The enclosures were incubated for 14 days at 100% RH humidity and at a temperature of 75° Fahrenheit. The enclosures serve as individual microclimates for each growing substrate set. By controlling the rate of gas exchange, humidity can be varied between RH 100%, inside an enclosure, and the exterior humidity, typically RH 30-50%. Each rectangular enclosure fully contained the substrate and inoculum preventing gaseous exchange. Opening the enclosures lids after 5 and 10 days allowed gaseous exchange. In some cases, lids included filter disks allowing continuous gas exchange.

After 14 days of growth, the enclosures were removed from the incubator. The loose fill particles and fibers having been bonded into a cohesive whole by the fungi's mycelium produced a rectangular panel with dimensions closely matching those of the growth enclosure. This panel was then removed from the enclosure by removing the lid, inverting the growth enclosure, and pressing gently on the bottom.

The mycelia bonded panel was then transferred to a drying rack within a convection oven. Air was circulated around the panel until fully dry, about 4 hours. Air temperature was held at 130 degrees Fahrenheit.

After drying, the now completed composite is suitable for direct application within a wall, or can be post processed to include other features or additions including water resistant skins, stiff exterior panel faces, and paper facings.

Within the above embodiment, the ratios and percentages of bulking particles, insulating particles, fibers, nutrients, inoculum, and water can be varied to produce composites with a range of properties. The materials expanded perlite compositions can vary from 5%-95% of the composite by volume. Other particles, including exfoliated vermiculite, diatomic earth, and ground plastics, can be combined with the perlite or substituted entirely. Particle sizes, from horticultural grade perlite to filter grade perlite are all suitable for composite composition and many different composite types can be created by varying the ratio of perlite particle size or vermiculite or diatomic earth particle size.

Rice hulls can compose anywhere from 5-95% of the composite material by volume. Fibers can compose from 1-90% of the material by volume. DGS can compose between 2-30% of the substrate by volume. The inoculum, when in the form of grain, can compose between 1-70% of the substrate by volume. The inoculum, when in other forms can comprise up to 100% of the substrate. Ground cellulose, sourced from waste paper, can compose from 1-30% of the substrate by volume.

Other embodiments may use an entirely different set of particles from either agricultural or industrial sources in ratios sufficient to support the growing of filamentous fungi through their mass.

Though not detailed in this embodiment, the engineered substrate can also contain elements and features including: rods, cubes, panels, lattices, and other elements with a minimum dimension 2 times larger than the mean diameter of the largest average particle size.

In this embodiment, the fungi strain *Pleurotus ostreatus* was grown through the substrate to produce a bonded composite. Many other filamentous fungi's could be used to produce a similar bonding result with differing final composite strength, flexibility, and water sorption characteristics.

In this embodiment, the substrate was inoculated using *Pleurotus ostreatus* growing on rye grain. Other methods of inoculation, including liquid spore inoculation, and liquid tissue inoculation, could be used with a similar result.

Incubation of the composite was performed at 100% RH humidity at 75° Fahrenheit. Successful incubation can be performed at temperatures as low as 35° Fahrenheit and as high as 130° Fahrenheit. RH humidity can also be varied to as low as 40%.

Drying was accomplished using a convection oven but other methods, including microwaving and exposing the composite to a stream of cool, dry air, are both viable approaches to moisture removal.

Figure 7:
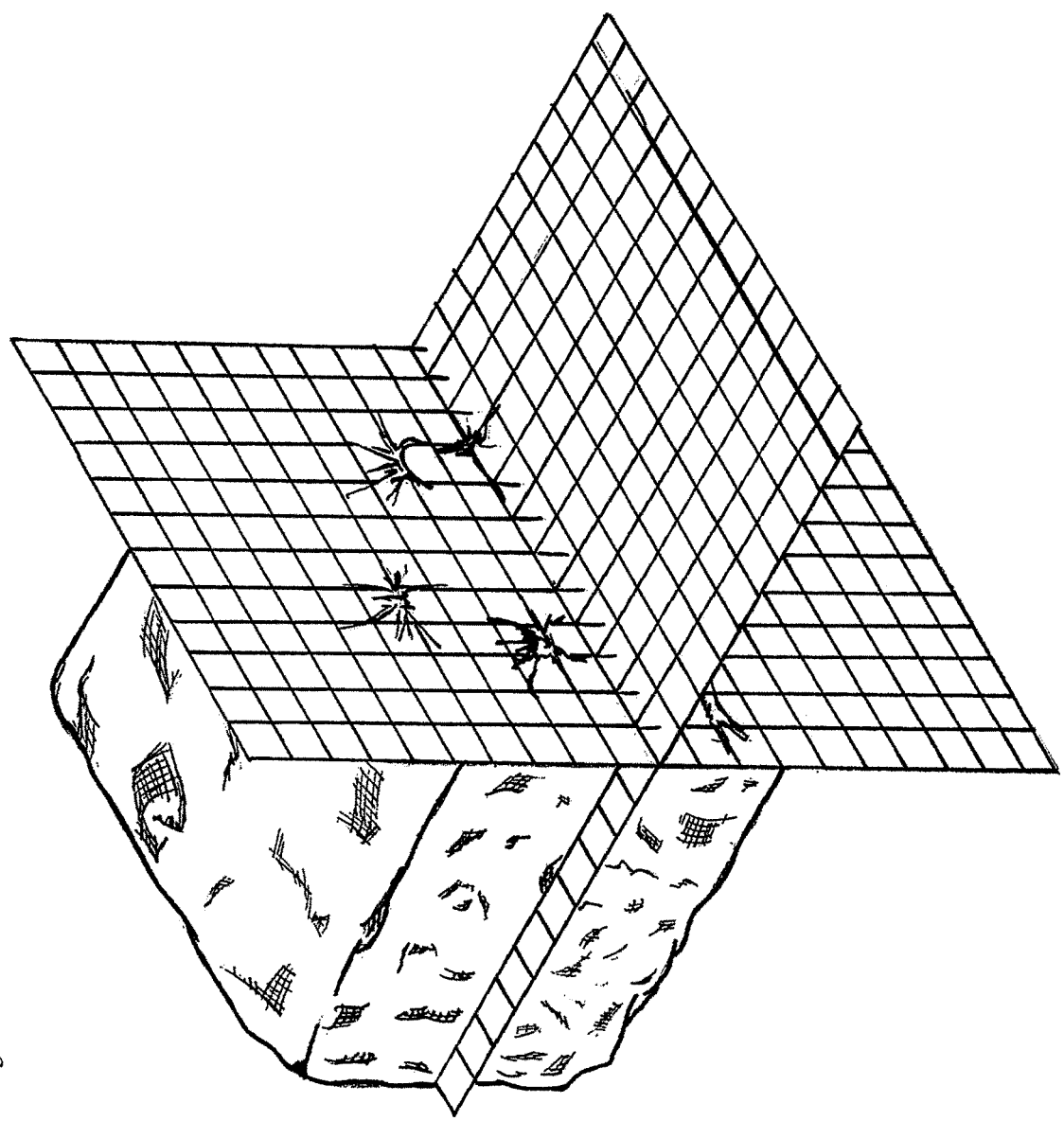
FIG. 7 illustrates a plastic lattice supporting mycelium growth in accordance with the invention.

Structure or Lattice for Mycelium Growth—FIG. 7

Mycelia based composites may be grown without the explicit use of a loose fill particle substrate. In fact, by creating a highly organized growth substrate, formations of mycelia composites can be created that might not normally arise when growth is allowed to propagate naturally through loose particles.

One way of adding an engineered structure to mycelium composites is to produce a digestible or non-digestible 3-d framework within which the mycelium grows. This framework may be formed from the group including: starch, plastic, wood, or fibers. This framework may be oriented orthogonally or oriented in other ways to produce mycelia growth primarily along the axis's of the grid. Additionally, this grid may be flexible or rigid. Spacing between grid members can range from 0.1 mm to upwards of 10 cm.

Growth along these engineered grids or lattices results in mycelium composites with highly organized hyphae strands allowing the design and production of composites with greater strength in chosen directions due to the organized nature of the supporting mycelia structure.

Such an arrangement also allows the development of organized mycelium structures composed primarily of hyphae rather than of bulking and nutritional particles.

To produce one embodiment of such a structure the following steps are taken:

Referring to FIG. 7, a three-dimensional lattice, formed of sets of 1 mm×1 mm plastic grids 14 oriented orthogonally, is coated in a mixture of starch and water. This mixture is composed of 50% starch, and 50% tap water by volume. These materials were sourced as organic brown rice flour, and tap water, from the Troy NY municipal water supply, respectively.

This lattice is placed on/in a bed of inoculum containing *Pleurotus ostreatus* on a suitable nutrient carrier. The lattice and inoculum bed are then placed in an environment held at the correct temperature, between 55-95 degrees Fahrenheit, and humidity, between 75% RH and 100% RH, to stimulate mycelia growth.

FIG. 7 shows a cutaway of a grid based mycelium composite. Only two intersecting grids are shown, but the composite would actually be composed of a series of grids extending axially spaced 1 mm apart. Grid squares have an edge length of 1 mm. Here, mycelium 8 is shown growing through the grids 14. This thickly formed mycelia mat forms the bulk of the volume of the composite.

The mycelium is grown over and through the grid producing a dense network of oriented hyphae. Over time, the hyphae will interweave producing a dense 3-D mat. After 1 to 2 weeks of growth, the grid is removed from the incubator and dried, using either a convection oven, or other means to remove the water from the mycelium mass. Once dried the mycelia composite can be directly used, or post processed for other applications.

Within this embodiment, the grid may or not provide the mycelia a nutrient source, but if nutrients are not provided within the grid framework, the grid must be placed in close proximity to an inoculum containing a nutrient source as to allow the fungi to transport nutrients into the grid based mycelium for further cellular expansion.

The invention thus provides a new method of producing grown materials. These materials may be flexible, rigid, structural, biodegradable, insulating, shock absorbent, hydrophobic, hydrophilic, non-flammable, an air barrier, breathable, acoustically absorbent and the like. All of the embodiments of this invention can have their material characteristics modified by varying the organism strain, nutrient source, and other particles, fibers, elements, or other items, included in the growth process.

Further, the invention provides a method of making a mycological material that can be used for various purposes, such as, for food production.

What is claimed is:

1. A method of making a mycological product comprising the steps of
   providing a framework; and
   growing mycelium on said framework in an environment held at a temperature and humidity to stimulate mycelia growth for a time sufficient for the mycelia growth to form a dense network of oriented hyphae on said framework.

2. The method as set forth in claim 1, wherein said framework is digestible.

3. The method as set forth in claim 1, which further comprises the step of
   coating said framework with a mixture of starch and water prior to said step of growing mycelium on said framework.

4. The method as set forth in claim 3, which further comprises the step of
   placing the coated framework on a bed of inoculum containing *Pleurotus ostreatus* on a nutrient carrier prior to said step of growing mycelium on said framework.

5. The method as set forth in claim 1, wherein said framework is a mesh.

6. The method as set forth in claim 1, wherein said framework is a lattice.

7. The method as set forth in claim 6, wherein said lattice is plastic.

8. The method as set forth in claim 1, wherein said framework is formed from the group of materials selected from starch, plastic, wood, or fibers.

9. The method as set forth in claim 1, wherein said framework is a grid oriented orthogonally or oriented in other ways to produce mycelia growth primarily along the axis of said grid.

10. The method as set forth in claim 9, wherein said grid is either flexible or rigid.

11. The method as set forth in claim 9, wherein said grid is placed in close proximity to an inoculum containing a nutrient source as to allow the mycelium to transport nutrients into the mycelia growth primarily along the axis of said grid for further cellular expansion.

12. The method as set forth in claim 9, wherein the mycelium is grown over and through the grid producing a dense network of oriented hyphae.

13. The method as set forth in claim 12, wherein the oriented hyphae interweave.

14. The method as set forth in claim 9, wherein said mycelia growth forms a mycelia mass, and the method further includes the step of drying the grid so as to remove water from the mycelia mass.

15. The method as set forth in claim 14, further including a step of postprocessing.

16. The method as set forth in claim 1, wherein said framework is three dimensional.

17. The method as set forth in claim 1, wherein said framework is provided in close proximity to an inoculum containing a nutrient source.

* * * * *